United States Patent [19]

Allen et al.

[11] Patent Number: 6,074,183
[45] Date of Patent: Jun. 13, 2000

[54] PERISTALTIC SYSTEM AND METHOD FOR PLASMA SEPARATION AND BLOOD DISPENSATION

[75] Inventors: Michael P. Allen, Los Altos; Stoughton L. Ellsworth, Palo Alto; Lawrence M. Ensler, Los Altos; Kumar Subramanian, Pleasanton, all of Calif.

[73] Assignee: First Medical, Inc.

[21] Appl. No.: 09/104,887

[22] Filed: Jun. 25, 1998

Related U.S. Application Data

[63] Continuation-in-part of application No. 08/839,879, Apr. 16, 1997, abandoned, which is a continuation of application No. 08/386,242, Feb. 9, 1995, abandoned.

[51] Int. Cl.[7] ................................................ F04B 43/12
[52] U.S. Cl. ............................ 417/477.2; 210/416.1; 417/477.9
[58] Field of Search ............................ 604/151, 153; 417/53, 477.1, 477.2, 477.9–477.12; 422/100, 102, 104; 436/177, 178; 210/416.1, 541, 542, 645, 650, 767; 128/214.2

[56] References Cited

U.S. PATENT DOCUMENTS

| | | | |
|---|---|---|---|
| 4,025,241 | 5/1977 | Clemens | 417/477.11 |
| 4,201,406 | 5/1980 | Dennehey et al. | 128/214.2 |
| 5,057,081 | 10/1991 | Sunderland | 417/477.2 |
| 5,213,483 | 5/1993 | Flaherty et al. | 417/477.2 |
| 5,460,493 | 10/1995 | Deniega et al. | 417/477.9 |
| 5,564,915 | 10/1996 | Johnson | 417/477.9 |

Primary Examiner—Joseph W. Drodge
Attorney, Agent, or Firm—Townsend and Townsend and Crew LLP

[57] ABSTRACT

A system for separating plasma from whole blood comprises a blood separation device and a blood separation driver. The blood separation device includes a flexible tube having a needle and shield at one end and a filter member at the other end. The needle may be used to access blood in a conventional blood collection device. The separation driver applies a peristaltic force to the flexible tube of the blood separation device, thus drawing blood from the collection device through the tube and to the filter member. The driver also includes a frame having a collar and clamp mechanism for supporting the inlet end of the flexible tube, thus allowing use of the blood driver without directly exposing it to the blood. Plasma may be collected from the filter element. The present invention also provides blood dispensing systems and methods for dispensing whole and pre-filtered blood. Such blood dispensing systems comprise a blood dispensing device and a blood dispensing driver.

13 Claims, 6 Drawing Sheets

PERISTALTIC SYSTEM AND METHOD FOR PLASMA SEPARATION AND BLOOD DISPENSATION

This application is a continuation-in-part of U.S. patent application Ser. No. 08/839,879, filed Apr. 16, 1997, now abandoned, which is a continuation of U.S. patent application Ser. No. 08/386,242, filed Feb. 9, 1995, now abandoned, each of which is incorporated herein by reference in its entirety for all purposes.

BACKGROUND OF THE INVENTION

1. Field of the Invention

The present invention relates generally to systems and methods for assaying biological samples. More particularly, the present invention relates to a system and method for separating plasma from whole blood and transferring the plasma to an analytical substrate or device. The present invention also pertains to a system and method for dispensing whole or filtered blood and transferring dispensed blood to an analytical substrate or device.

Many diagnostic markers and other analytes are best determined from patient blood samples. The ability to measure such markers and analytes directly in blood, however, is problematic because of the presence of blood cells, particularly red blood cells, in whole blood. Thus, a majority of analytical systems and methods intended for measuring blood markers and analytes rely on detection in a plasma or serum sample, not in a whole blood sample.

A wide variety of blood separation systems and methods have been developed over the years particularly for use in performing plasma and serum assays. Such systems may be generally categorized as centrifugal, chemical, and filtration. Centrifugal systems rely on centrifugation to remove cellular components from the blood. Chemical systems rely on antibodies, lectins, or the like, for binding and removing cellular components. Finally, filtration relies on chromatographic and/or size-exclusion filtration elements for separating the cellular blood components from the resulting plasma fraction.

The present invention is concerned in particular with filtration systems and methods for producing plasma from whole blood prior to performing an assay on the plasma. Heretofore, filtration elements have often been constructed integrally in assay devices, where blood is applied to the filter element and plasma is separated and flows to a reaction zone. Such systems, however, generally require that the whole blood be initially transferred from the standard blood collection device, such as a syringe or more commonly a vacuum collection tube, often using a transfer pipette. The need to use a transfer pipette is disadvantageous in several respects. It increases the assay procedure time and introduces a source of contamination and error. Equally important, the need to remove blood from the collection device in an intermediate transfer step increases the likelihood of that personnel performing the assay will be exposed to the blood.

For these reasons, it would be desirable to provide improved systems and methods for separating plasma from whole blood for use in plasma assays and assay devices. It would be particularly desirable if such systems and methods could eliminate the need to employ an intermediate transfer step between the blood collection device and the blood filtration device, such as the use of a transfer pipette. It would be particularly desirable if the methods and devices would permit the direct separation of plasma from blood in a totally closed system, including the blood collection device, which could be disposed of after use without release of blood or blood components from the closed system (other than the plasma which has been intentionally transferred to an assay system). Such methods and systems should further provide for accurate and precise (repeatable) measurement of the plasma being separated, as well as for direct transfer of the plasma to a test substrate, receptacle, or other assay system.

Various systems and methods for dispensing blood and producing a measured amount of blood have also been developed over the years for use in performing blood assays. As with the plasma separation systems discussed above, systems and methods for dispensing blood typically require that the blood be initially transferred from a standard blood collection device, such as a syringe or vacuum collection tube, often using a transfer pipette. This transfer process is disadvantageous because it increases the assay procedure time and the possibility that personnel performing the assay will be exposed to the blood. Such process also introduces a source of contamination and error. It would thus be desirable to provide improved systems and methods for dispensing a measured volume of blood for use in blood assays and assay devices. It would be especially desirable if such systems and methods did not require an intermediate transfer step (e.g., as described above) to transfer blood from the collection device to the blood dispensing device. It would also be advantageous if such systems and methods would allow direct dispensation of blood from a totally closed system to protect against inadvertent release of the blood or bloods components. In addition, it would useful if such systems and methods would provide for precise measurement of the dispensed blood and direct transfer of dispensed blood to a test substrate or other assay device.

2. Description of the Background Art

U.S. Pat. No. 4,086,060, describes a blood filtering device which is employed between a blood collection device and a plasma receptacle. U.S. Pat. Nos. 4,980,297 and 4,970,052, describe plasma transfer devices which include needles for accessing blood collection devices and the rubber stoppers on the collection devices. The following patents describe other plasma separation systems and devices: U.S. Pat. Nos. 5,275,731; 5,262,049; 5,151,184; 4,957,637; 4,828,716; and 3,814,258. Filter elements for separating plasma from whole blood in combination with absorptive pads are shown in a number of patents, including U.S. Pat. Nos. 5,262,067; 5,132,086; 5,110,724; 4,987,085; 4,933,092; 4,816,224; 4,753,776; 4,477,575; and 3,663,374. Other patents showing assay devices including separation membranes and absorptive pads include U.S. Pat. Nos. 4,678,757; 4,952,516; 4,999,163; 5,000,922; 5,135,719; 5,186,843; 5,266,219; and 5,308,483.

SUMMARY OF THE INVENTION

According to the present invention, systems and methods are provided for dispensing whole or pre-filtered blood and transferring the dispensed blood to an analytical device or substrate. The system includes both a blood dispensing device and a blood dispensing driver. The blood dispensing device is connected directly to a conventional blood collection device, such as a vacuum collection device, and provides a fluid flow path for dispensing blood from the collection device. The blood dispensing driver acts on the blood dispensing device to induce blood flow from an exit port in the dispensing device. A particular advantage of the present invention is that the assembly of the blood dispensing device and the blood collection device is entirely closed, except for the exit port. Thus, all blood and blood components other than the transferred blood remain contained and confined within the combination of the blood dispensing device and collection device which may be disposed of after the dispensing procedure in order to reduce the risk of exposing the operating personnel to the blood. Moreover, the risk of contamination is reduced since the blood driver is not exposed directly to the blood which remains contained within the combination of blood collection and dispensing devices.

In a first aspect, the present invention provides methods for dispensing blood which comprise introducing blood into an inlet end of a flexible tube having an internal lumen. The first and second opposed clamping elements of a driver assembly are clamped to removably secure the flexible tube in the driver assembly. Blood is caused to flow from the inlet end to an outlet end of the flexible tube by rotating a drive wheel mounted on the first clamping element to apply peristaltic force to an exterior surface of the flexible tube while the tube is secured in the driver assembly. Blood is directed through the outlet end of the tube, resulting in the dispensation of blood. Preferably, the peristaltic force is applied by rotating a drive wheel in the driver assembly to apply the peristaltic force. After a preselected volume of blood has been dispensed, the flexible tube can be removed from the driver and disposed of.

In a second aspect, the invention provides methods for dispensing blood present in a receptacle which comprise connecting an inlet end of a flexible tube to the blood receptacle, such as a blood collection device, so that blood can flow into an internal lumen of the tube. The flexible tube is removably secured in a driver assembly, which includes a frame and a clamping assembly mounted on the frame. The clamping assembly comprises first and second opposed clamping elements which are spaced apart and free to move independently of one another by translating one or both of the clamping elements to selectively secure and release the tube. A drive wheel in the driver assembly is rotated to apply peristaltic force to an exterior surface of the flexible tube, thus causing blood flow from the receptacle, through the internal lumen of the flexible tube, and to an outlet end of the tube. Blood is directed through the outlet end of the tube to dispense the blood.

In a preferred aspect, the flexible tube is connected to the receptacle by piercing a needle at the inlet end of the tube through a septum or stopper in the receptacle, e.g., a conventional blood collection device. In a preferred aspect, the tube is secured in the driver assembly by releasably clamping the tube in a vertical orientation with the inlet end above and the outlet end below. In some such methods, the tube is clamped at a first location near the inlet end and a second location near the outlet end with a portion of the tube intermediate said ends being exposed to the drive wheel. In a preferred aspect, the drive wheel engages the flexible tube against an arcuate surface to achieve the desired peristaltic flow through the lumen of the tube.

In another preferred aspect, after a desired preselected volume of blood has been dispensed, the intact assembly of the tube and blood receptacle can be removed from the driver assembly and disposed of. In yet another preferred aspect, the inlet end of a second flexible tube assembly is connected to a second receptacle and the resulting assembly removably secured in the same driver assembly by translating one or both clamping elements to selectively secure and release the second tube, and again rotating the drive wheel to apply peristaltic force to the exterior surface of the second tube in order to cause blood to flow from the receptacle to achieve blood dispensation. Advantageously, the driver assembly is never exposed to whole blood or blood components.

A preferred blood dispensing device comprises a flexible tube having an inlet end, an outlet end, and a blood flow lumen therebetween. A needle structure is disposed at the inlet end of the flexible tube. The needle structure has a lumen which feeds into the blood flow lumen of the flexible tube. The flexible tube provides a lumen to permit blood flow from the needle (which may be used to access a conventional blood collection device as described above) and through the outlet end of the tube, causing blood to be dispensed from the outlet end of the tube. The flexible tube may be inserted into a peristaltic or other driver assembly to induce the desired blood flow. In one preferred aspect, the needle structure has an axial passage which is aligned with the blood flow lumen of the flexible tube. Optionally, a receptacle shield may be attached to the inlet end of the flexible tube to surround the needle structure. The shield will be sized to receive a conventional blood collection device.

A blood dispensing driver according to the present invention comprises a frame and a clamping assembly on the frame for removably securing a blood dispensing device. The blood dispensing device comprises a flexible tube having an inlet end and an outlet end. The clamping assembly comprises two opposed clamping elements that are translatably coupled to the frame for removably securing the flexible tube in the blood dispensing driver. The blood dispensing driver further comprises a peristaltic drive wheel mounted on the first clamping element to engage the flexible tube between the peristaltic drive wheel and the second clamping element when the blood dispensing device is secured in the clamping assembly, wherein rotation of the drive wheel induces blood to flow from the inlet end to the outlet end of the flexible tube, causing blood to be dispensed.

A blood dispensing device such as that described above may be removably secured in the clamping assembly of the blood dispensing driver. When the blood dispensing device is secured in the clamping assembly, the flexible tube is engaged between the drive wheel and the second clamping element, and rotation of the drive wheel can induce blood to flow from the inlet end to the outlet end of the tube.

In a preferred aspect, the drive wheel of the blood dispensing driver comprises a plurality of peripherally spaced-apart rollers. Preferably, the frame of the blood dispensing driver comprises a collar for supporting the inlet end of the flexible tube in a vertical manner.

In another preferred aspect of the blood dispensing driver, the frame further comprises one or more rods which extend laterally from the collar. At least one of the opposed clamping elements is translatably mounted on the one or more rods. Additionally, the dispensing driver preferably comprises at least one motor for translating one or both of the clamping elements to selectively secure and release the flexible tube when it is placed in the collar.

In yet another preferred aspect, the second clamping element of the clamping assembly of the blood dispensing driver has an arcuate surface which is aligned with the drive wheel, wherein the flexible tube is captured between the drive wheel and the arcuate surface.

The present invention still further provides blood dispensing systems comprising both a blood dispensing device and a blood dispensing driver. The blood dispensing device includes a flexible tube having an inlet end, an outlet end, and a tubular lumen. A needle structure is disposed at an inlet end of the flexible tube. The blood dispensing driver of such blood dispensing systems includes a frame, a clamp mounted on the frame for removably securing the blood dispensing device, and a peristaltic drive wheel on the frame. The peristaltic drive wheel engages an exterior surface of the flexible tube to induce blood flow through the tubular lumen of the tube when the tube is secured in the clamp. The clamp comprises first and second opposed clamping elements. At least one of the clamping elements is translatably coupled to the frame so that the clamping element can be translated to selectively secure the blood dispensing device. The preferred aspects of both the blood dispensing device and the blood dispensing driver are generally described above.

In another aspect, the invention provides a blood dispensing system comprising a blood dispensing device and a blood dispensing driver. The blood dispensing device comprises a flexible tube having an inlet end and an outlet end, wherein the inlet end of the tube has a needle structure. The blood dispensing driver comprises a frame, wherein the frame comprises a collar for supporting the inlet end of the flexible tube and one or more rods which extend laterally from the collar; a clamp for removably securing the blood dispensing device, wherein said clamp comprises first and second opposed clamping elements at least one of which is translatably mounted on the rods; a peristaltic drive wheel which is mounted on at least one of the clamping elements and engages an exterior surface of the flexible tube to pass blood through a lumen thereof when the tube is secured in the clamp; and at least one motor for translating one or both of the clamping elements to selectively secure and release the flexible tube when placed in the collar. In a preferred aspect, one of the clamping elements has an arcuate surface which is aligned with the drive wheel, wherein the flexible tube is captured between the drive wheel and the arcuate surface.

In yet another aspect, the invention provides a blood dispensing system comprising a blood dispensing device, which includes a flexible tube having an inlet end and an outlet end, and a needle structure at the outlet end of the flexible tube, and a blood dispensing driver. The blood dispensing driver includes a frame; a clamping assembly on the frame comprising first and second opposed clamping elements, wherein at least one of said clamping elements moves translatably on the frame, for removably securing the blood dispensing device; a peristaltic drive wheel mounted on the first clamping element, wherein said drive wheel comprises a plurality of rollers; and at least one motor for moving one or both of the clamping elements to selectively capture the tube against the rollers to induce blood flow through the outlet end of the tube when the drive wheel is rotated to dispense blood.

In still another aspect, the invention provides a blood dispensing system comprising a blood dispensing device, which includes a flexible tube having an inlet end and an outlet end and a needle structure at the inlet end of the flexible tube, and a blood dispensing driver. The blood dispensing driver comprises a clamping assembly, which comprises first and second opposed clamping elements to removably secure the tube in the dispensing driver, a peristaltic drive wheel having an axis of rotation and mounted on the first clamping element, wherein said drive wheel comprises a plurality of rollers, and at least one motor for moving one or both of the clamping elements transversely to the axis of rotation of the drive wheel to engage the tube between the drive wheel and the second clamping element.

In another aspect, the present invention provides a method for dispensing blood. Such method comprises providing a blood dispensing device which comprises a flexible tube having an inlet end, an outlet end, and a blood flow lumen therebetween. A needle structure is positioned at the inlet end of the flexible tube. The needle structure has a lumen which feeds into the blood flow lumen of the flexible tube, wherein blood flowing from the blood flow lumen passes through the outlet end of the flexible tube. Such method further comprises providing a blood dispensing driver which includes a frame, a clamping assembly mounted on the frame, and a peristaltic drive wheel. The clamping assembly includes two opposed clamping elements at least one of which moves translatably on the frame to selectively secure the blood dispensing device. Such method further comprises connecting the inlet end of the flexible tube to a receptacle for blood so that blood flows into an internal lumen of the tube, removably securing the blood dispensing device in the blood dispensing driver by using the clamping assembly, directing blood from the outlet end of the flexible tube through the outlet end of the tube to dispense blood, and removing and disposing of an intact assembly of the blood dispensing device and receptacle after a desired volume of blood has been dispensed, whereby the risk of inadvertent blood loss is minimized.

DESCRIPTION OF THE SPECIFIC EMBODIMENTS

The present invention comprises systems and methods for providing plasma and dispensing blood for subsequent analysis in order to qualitatively or quantitatively determine the presence of target markers, analytes, enzyme activities, proteins, small molecules, infectious organisms, drugs, and the like. Plasma consists of whole blood from which the blood cells, including both red blood cells and white blood cells, have been separated. Generally, blood proteins and other macromolecules, including the clotting proteins, immunoglobulins, and other blood factors and non-cellular components, remain in the plasma. In particular, the present invention provides for filtration of cellular components from whole blood to provide plasma as will be described in more detail hereinbelow. All blood components substantially smaller than the cellular components will remain in the separated plasma. Thus, virtually any test which can be performed on plasma can utilize plasma obtained by the systems and methods described below.

Separation of cellular components from whole blood according to the present invention will generally be obtained by two-stage filtration with a chromatographic filter element in series with a size-exclusion filter element. The chromatographic filter element will typically be a depth filter, often including two or more separate layers. The chromatographic filter element performs an initial separation of cellular components from the plasma based on chromatographic principles, i.e. the plasma will travel through the chromatographic element at a rate faster than the blood cells which, because of their size are preferentially slowed. The chromatographic filter element can be composed of any conventional filter medium, such as glass fiber, polyester fiber, plastic fiber, metal fiber, composite cellulose and synthetic fiber, nylon mesh, polyester mesh, synthetic fabric, and the like. A preferred chromatographic filter element material is glass fiber. The area and depth of the chromatographic filter element will depend on the volume of plasma to be separated from the applied whole blood, as described in more detail below. The chromatographic filter element will have a volume which is sufficiently large to retain blood cells and prevent blockage of the size-exclusion membrane so that a desired volume of plasma can pass through the combined filter member. Typically, the volume of the chromatographic filter element will be in the range from 25 mm$^3$, preferably from 25 mm$^3$ to 700 mm$^3$. The depth of the chromatographic filter element will typically be in the range from 1 mm to 10 mm, usually from 2 mm to 6 mm.

The size-exclusion filter membrane will have a pore size selected to exclude the passage of cells, typically being less than 7 $\mu$m, preferably being in the range from 0.1 $\mu$m to 7 $\mu$m, more preferably being from 0.4 $\mu$m to 3 $\mu$m. The size-exclusive membrane can be composed of any conventional membrane material, such as nitrocellulose, cellulose acetate, regenerated cellulose, polycarbonate, polyamide, and the like. A preferred size-exclusion filter membrane is polycarbonate.

In a preferred design, the size-exclusion membrane may be composed of or coated with a hydrophobic material, such as hydrophilic track-etched polycarbonate. A hydrophobic membrane surface will create a barrier which inhibits the passage of plasma unless a threshold positive pressure (referred to as the bubble point) is exceeded. Thus, the membrane can provide a valving effect where leakage of plasma is inhibited in the absence of pressure provided by the pump driver. This is a particular advantage in that the blood and plasma remaining in the blood separation device will remain contained to protect personnel from exposure to the blood and plasma before and after the separation is accomplished.

Materials and constructions for two-stage filter systems suitable for use in the present invention are described in U.S. Pat. No. 3,663,374, the full disclosure of which is incorporated herein by reference.

The filter members are provided as part of a blood separation device which includes a flexible tube having a needle or other access element at its inlet end and the filter (present in a filter member housing) at its outlet end. The flexible tube may be composed of any resilient material which is compatible with blood flow, particularly being non-thrombogenic and free from contaminants which might be released into the blood or plasma. Suitable materials include silicone rubber, latex, polyvinylchloride (PVC), Santoprene®, neoprene, and the like.

The dimensions of the flexible tube are not critical. For use with the blood separation driver described hereinafter, however, the tube will usually have a length in the range from about 10 mm to 100 mm, preferably from 20 mm to 50 mm. The tube will have an internal lumen for transporting blood having a diameter in the range from 0.5 mm to 5 mm, preferably from 1 mm to 3 mm. Typically, the external diameter of the tube will be from 1 mm to 7 mm, preferably from 1.5 mm to 5 mm. The tube will usually have uniform dimensions along its length, but such uniformity is not essential.

The access device will typically be a needle, hypotube, or other structure capable of piercing a rubber stopper or septum of the type found in conventional blood collection devices, such as vacuum collection devices, e.g. Vacutainers® available from Becton-Dickinson, Franklin Lakes, N.J. In particular, the needle structures will provide both for piercing of the septum and provide for an internal lumen to permit blood flow from the blood collection device into the flexible tube. Usually, but not necessarily, the lumen of the needle will be coaxially aligned with the lumen of the flexible tube. The filter member will be secured to the outlet end of the flexible tube and will further include an outlet port to permit outflow of separated plasma from the blood separation device. Optionally, a cylindrical shield is secured at the inlet end of the flexible tube and disposed about the needle or other access element. The shield has a length in the range from 20 mm to 75 mm and an internal diameter in the range from 15 mm to 30 mm and defines a receptacle for receiving and protecting the blood collection device when it is attached to the blood separation device. Optionally, the shield may be integral with the needle.

The blood separation driver can be any system capable of receiving and holding the blood separation device which can further induce blood flow through the device. In the broadest aspect of the present invention, the separation driver can induce blood flow by applying an external vacuum or internal pressurization within the assembly of the blood separation device and the blood collection device. It will be appreciated that internal pressurization within the blood collection device will cause outflow of blood through the blood separation device and the production of plasma. Alternatively, an external vacuum can draw blood flow from the blood collection device through the blood separation device. Internal pressurization and external vacuum, however, are generally less preferred since they increase the risk of loss of containment, particularly in the case of internal pressurization where the pressure source must be connected directly to the blood-containing collection device.

Preferred blood separation drivers according to the present invention will employ a mechanism for externally applying a peristaltic force to the flexible tube of the blood separation device described above. In the exemplary system, a peristaltic force is applied by a drive wheel having a plurality of rollers which contact and squeeze the flexible tube as the drive wheel is rotated. The successive and progressive squeezing of the tube results in positive displacement of blood through the tube.

Figure 1:
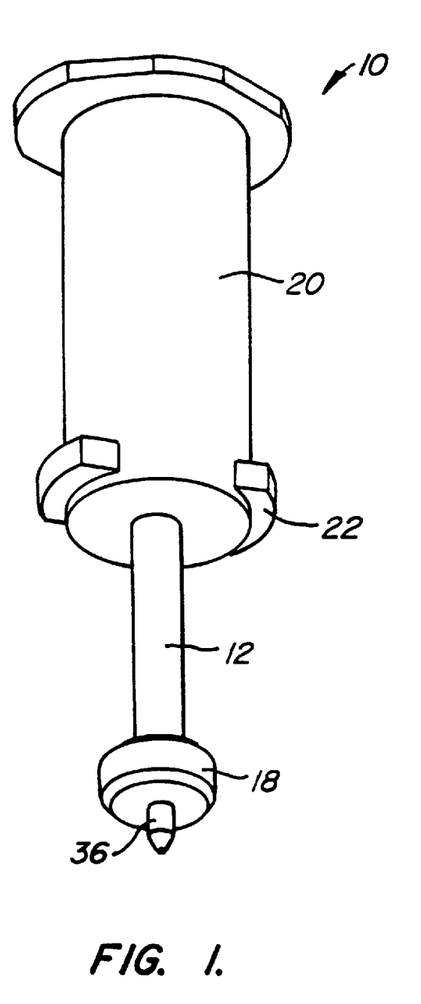
FIG. 1 is a perspective view of a blood separation device constructed in accordance with the principles of the present invention.
Figure 2:
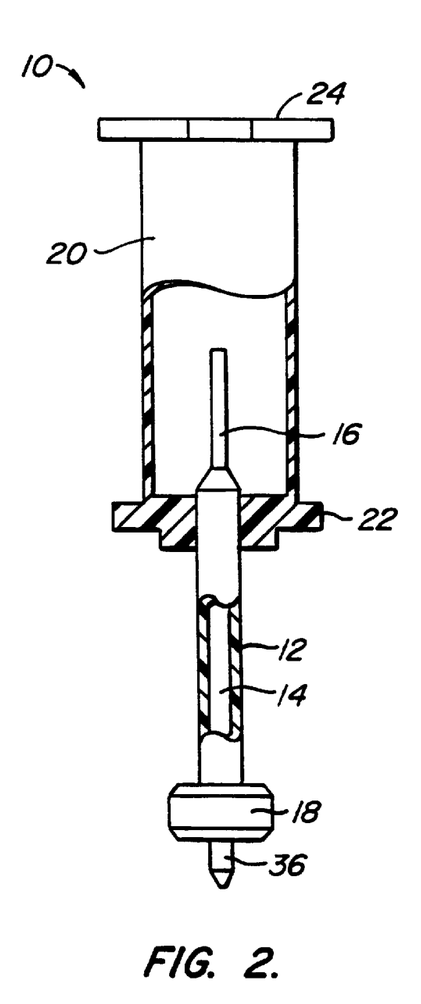
FIG. 2 is an elevational view of the blood separation device of FIG. 1, shown with portions broken away.
Figure 3:
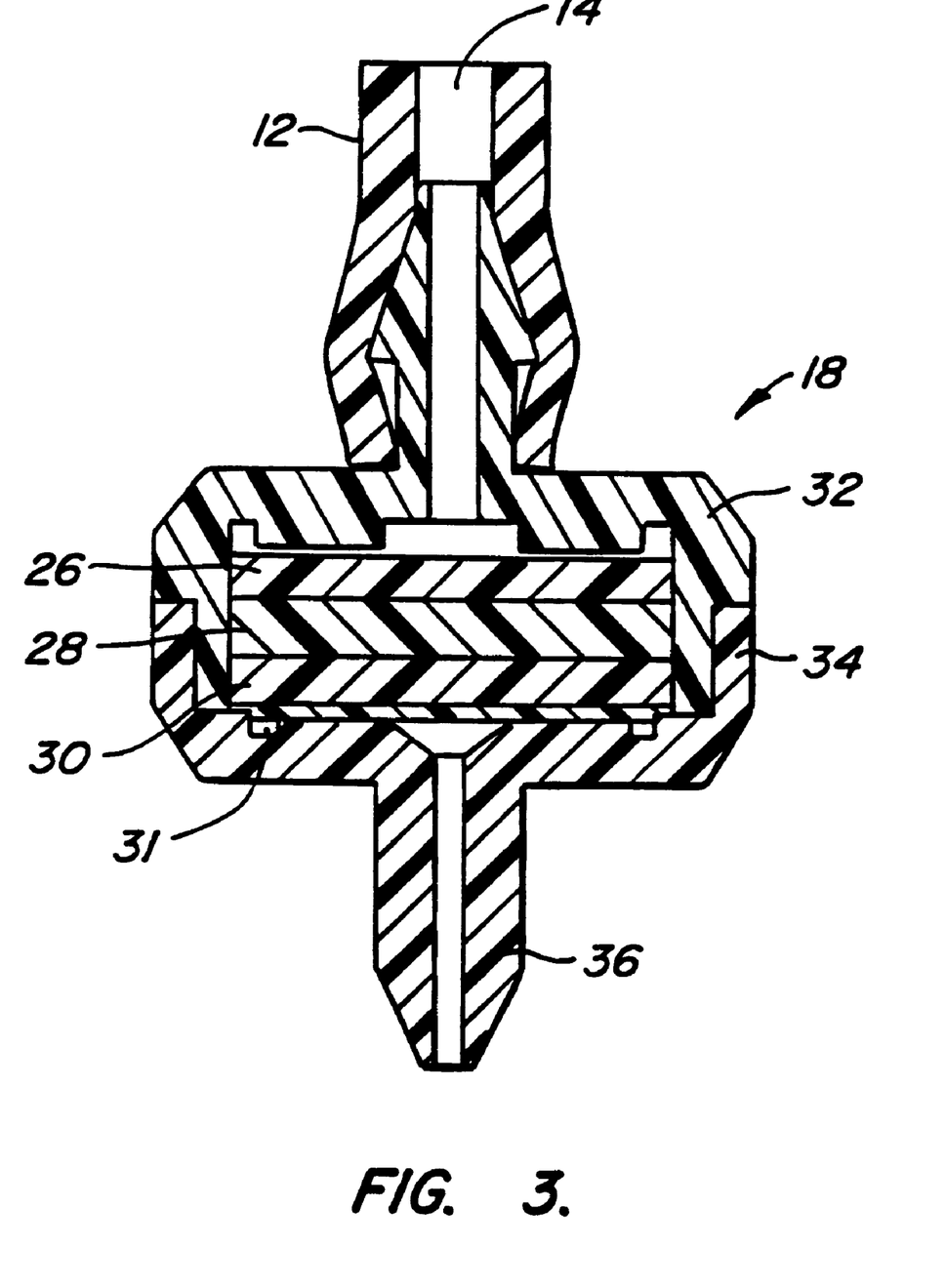
FIG. 3 is a detailed view of the filter element of the blood separation device of FIGS. 1 and 2, shown in section.

Referring now to FIGS. 1–3, a blood separation device 10 comprises a flexible tube 12 having an internal lumen 14. A needle assembly 16 is attached at an inlet end of the flexible tube 12 and a filter member 18 is attached at an outlet end of the flexible tube 12. A shield 20 having a flange 22 at its base is disposed around the needle assembly 16 and attached to the inlet end of flexible tube 12. The shield 20 is opened at its upper end 24 so that it can receive a conventional blood collection device, such as a vacuum collection device, which can be introduced over the needle assembly 16, as described in more detail hereinafter.

The filter assembly 18 houses a three-layer filter element including individual glass fiber layers 26, 28, and 30 and final size-exclusion membrane 31 below the glass fiber layers. The filter assembly 18 includes two separable halves 32 and 34 to facilitate assembly after the glass fiber layers 26, 28 and 30 and size-exclusion membrane 31 have been introduced. A plasma outlet port 36 is provided at the base of the filter member 18 to permit directed transfer of the plasma to a desired assay device or substrate. Preferably, the size-exclusion membrane 31 is sealed tightly against the bottom glass fiber layer 30 to inhibit leakage of blood and plasma past the membrane.

Figure 6:
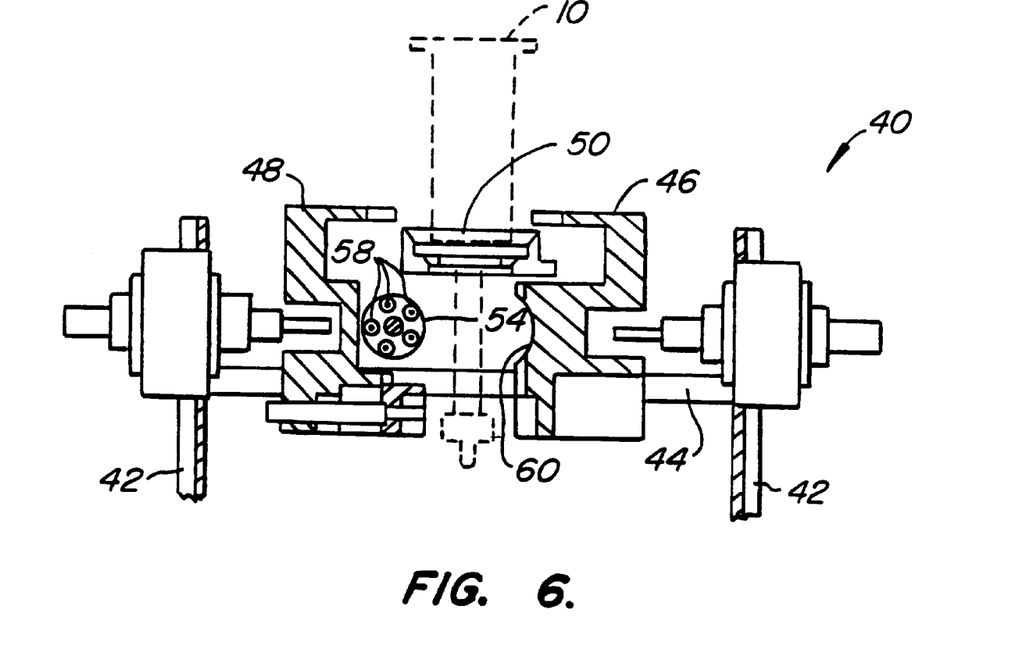
FIG. 6 is a detailed view of the opposed clamping elements and peristaltic drive element of the blood separation driver of FIG. 5, shown with the clamping elements in their open (spaced-apart) configuration.
Figure 7:
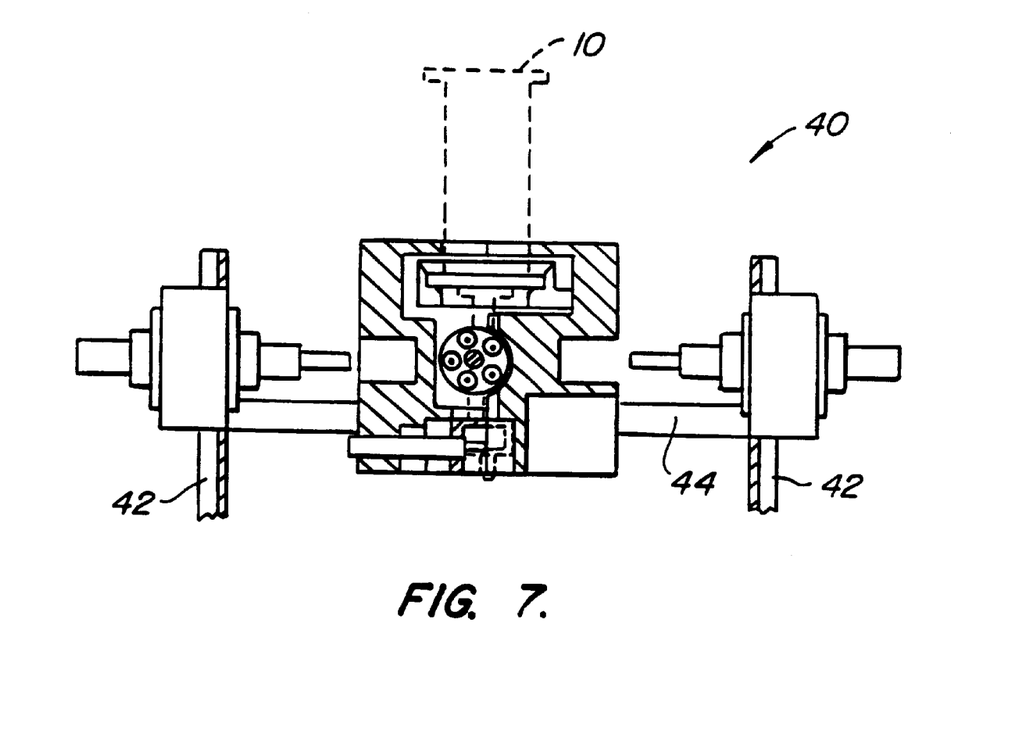
FIG. 7 is a view similar to FIG. 6, shown with the clamping elements in their closed configuration.
Figure 8:
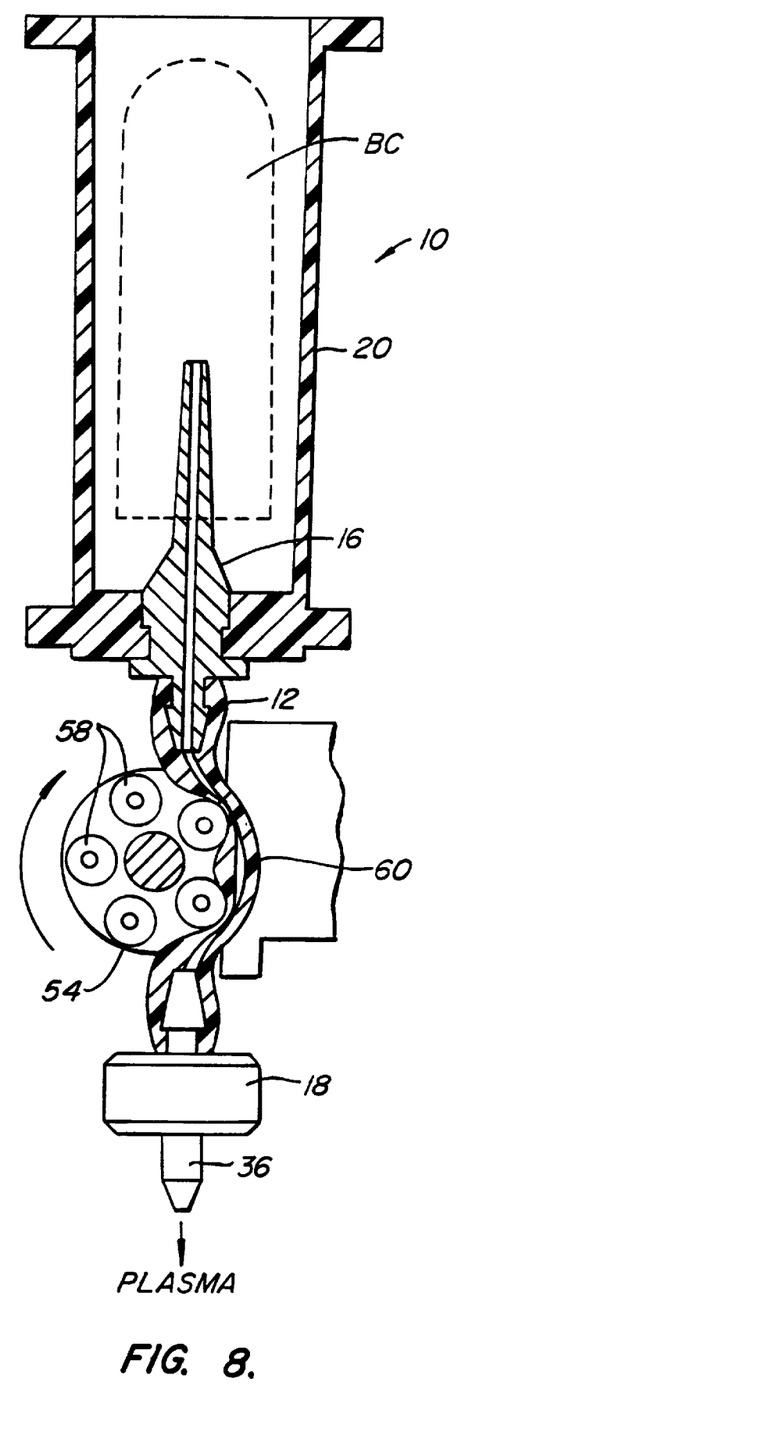
FIG. 8 is a detailed view of the peristaltic driver of the blood separation driver of FIG. 5, shown with a blood separation device in place.

The blood separation driver 40 is illustrated in FIGS. 4–7. The blood separation driver 40 includes frame members 42, support rods 44 extending between the frame members 42, and opposed clamping elements (or clamp elements) 46 and 48 which are translatably coupled to the frame and mounted to translate freely relative to each other over the support rod 44. A support collar 50 is fixedly mounted on the support rods 44 and includes a central aperture 52 for removably receiving a blood separation device 10 of the type described above. A peristaltic drive wheel 54 is mounted on the clamping element 48, as best observed in FIG. 5. DC gear motor 56 is directly connected to the drive wheel 54 so that a plurality of rollers 58 on the drive wheel 54 can be incrementally turned relative to the clamping elements. As best observed in FIG. 6, an arcuate recess 60 is provided in the face of the opposed clamping element 46. When the opposed clamping elements 46 and 48 are brought together, as illustrated in FIG. 7, the rollers 58 of drive wheel 54 are received within the arcuate recess 60, leaving a narrow annular region therebetween for receiving the flexible tube 12 of the blood separation device 10, as best illustrated in FIG. 8. At least one motor 56 is employed for moving one of both of the clamping elements 46 and 48 to selectively capture the flexible tube 12 against the rollers 58 to induce blood flow through the outlet end of the tube 12 when the drive wheel 54 is rotated to dispense blood. In one aspect, the drive wheel is mounted on the first clamping element 48, and one or both of the clamping elements 46 and 48 are moved normal to the axis of the drive wheel 54 by at least one motor 56 so as to engage the flexible tube 12 between the drive wheel 54 and the second clamping element 46.

The blood separation device 10 may be placed in the support collar 50 of the blood separation driver 40 when the opposed clamping elements 46 and 48 are spaced apart, as best observed in FIG. 6. After the blood separation device is properly positioned, the opposed clamping elements will be brought together and will capture the filter element in the lower portion thereof, as illustrated in FIG. 7. By anchoring the flexible tube 12 at both its inlet end (via the collar 50) and its outlet end (via capture of the filter member 18), the flexible tube will be held generally in place as it is captured between the rollers 58 of drive wheel 54 and the arcuate recess 60 of clamp 46. By then rotating the drive wheel 54, as illustrated by the arrow in FIG. 8, the peristaltic force which draws blood from a blood collection device (BC) through the tube 12 with plasma flowing out from the port 36 of filter element 18. When a desired volume of blood plasma has been produced, rotation of the drive wheel 54 can be stopped, the opposed clamping elements 46 and 48 are moved apart, and the assembly of the blood collection device (BC) and blood separation device 10 is removed from the driver. The assembly of the blood collection device (BC) and blood separation device 10 will be fully closed, except for the plasma outlet port 36. The presence of the size-exclusion membrane 31, however, will inhibit loss of plasma from the port. Thus, the assembly can be disposed of as an integral unit, reducing the risk of exposure of the blood to personnel using an associated analytical system. Moreover, the analytical system itself will have the minimum exposure to blood and blood components.

In another embodiment, the present invention provides methods and systems for dispensing blood for subsequent analysis, including those analyses described above. In particular, the present invention provides systems and methods for dispensing a desired volume of blood. Virtually any type of blood, including whole blood, filtered blood, and plasma that has been previously separated from blood, can be dispensed by using with the systems and methods of the present invention.

The blood dispensing system comprises a blood dispensing device and a blood dispensing driver. The blood dispensing driver can be any system capable of receiving and holding the blood dispensing device which can further induce blood flow through the device, including the embodiments described above for the blood separation driver which may function in an alternative manner to dispense whole or filtered blood or plasma that has already been separated from blood. The preferred aspects and embodiments of the blood dispensing driver are as described above for the blood separation driver.

In one aspect, for example, the blood dispensing driver includes a frame and a clamp mounted on the frame for removably securing the blood dispensing device. The clamp comprises first and second opposed clamping elements, wherein at least one of the clamping elements is translatably coupled to the frame for translating said clamping element to selectively secure the blood dispensing device. The blood dispensing drive further includes a peristaltic drive wheel on the frame which engages an exterior surface of the flexible tube to pass blood through a lumen thereof when the tube is secured in the clamp. The blood dispensing system may also include a receptacle shield which is attached to the inlet end of the flexible tube and which surrounds the needle structure as described above with regard to the blood separation system. Preferred aspects of the flexible tube, needle structure, and receptacle shield are as described in detail above for the blood separation system.

In another preferred aspect, the frame of the blood dispensing system comprises a collar for supporting the inlet end of the flexible tube. In still another preferred aspect, the frame further comprises one or more rods, which extend laterally from the collar, wherein at least one of the clamping elements is translatably mounted on the rods, and wherein the blood dispensing driver further comprises at least one motor for translating one or both of the clamping elements to selectively secure and release the flexible tube when placed in the collar. In another preferred aspect, the drive wheel of the dispensing system is mounted on the first clamping element and the second clamping element has an arcuate surface which is aligned with the drive wheel, wherein the flexible tube is captured between the drive wheel and the arcuate surface. In yet another aspect, the drive wheel comprises a plurality of peripherally spaced-apart rollers.

The blood dispensing system may be connected to a blood receptacle, such as a blood collection device, via the blood dispensing device, as described above for the blood separation system. The intact assembly of the blood dispensing device and receptacle comprises a totally closed system, which prevents loss of blood or blood components except those that are intentionally dispensed. This intact assembly may be removed and disposed of an after a measured amount of blood has been dispensed. In this way, the risk of inadvertent blood loss and the risk of exposure of the blood to operating personnel is minimized.

The preferred aspects and embodiments of the blood dispensing device include those described in detail above for the blood separation device, except that no filter elements are employed in the filter assembly for separating plasma from blood. Without filter elements, the blood separation devices discussed above can function as a blood dispensing device. In this aspect, the blood dispensing driver acts on the blood dispensing device, which includes a flexible tube and needle structure as described above with regard to the blood separation device, to induce blood flow through the blood dispensing device and to dispense a measured amount of blood through an outlet end of the flexible tube. The flexible tube and needle structure of the blood dispensing device have the same characteristics and preferred aspects as described above, respectively, for the tube and needle structure employed with the blood separation device. The blood dispensing system may be used to dispense a selected volume of whole or filtered blood (or plasma that has been previously separated from blood). The dispensed blood may then be transferred to a desired analytical device or substrate.

Figure 3A:
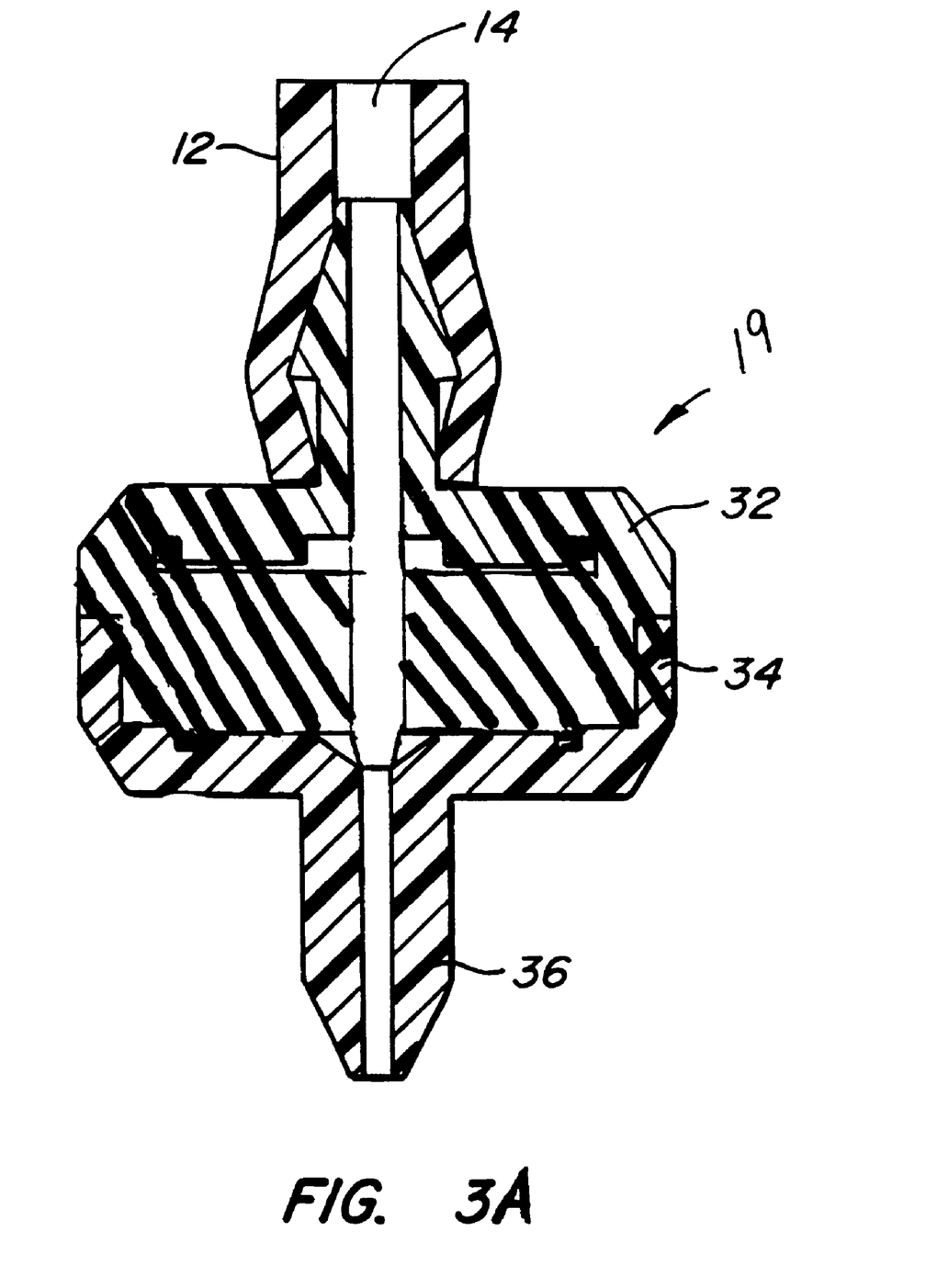
FIG. 3A is a detailed view of a dispensing assembly of the blood separation device of FIGS. 1 and 2, shown in section, for use in accordance with the principles of the blood dispensing systems, blood dispensing devices, drivers, and methods of the present invention.
Figure 4:
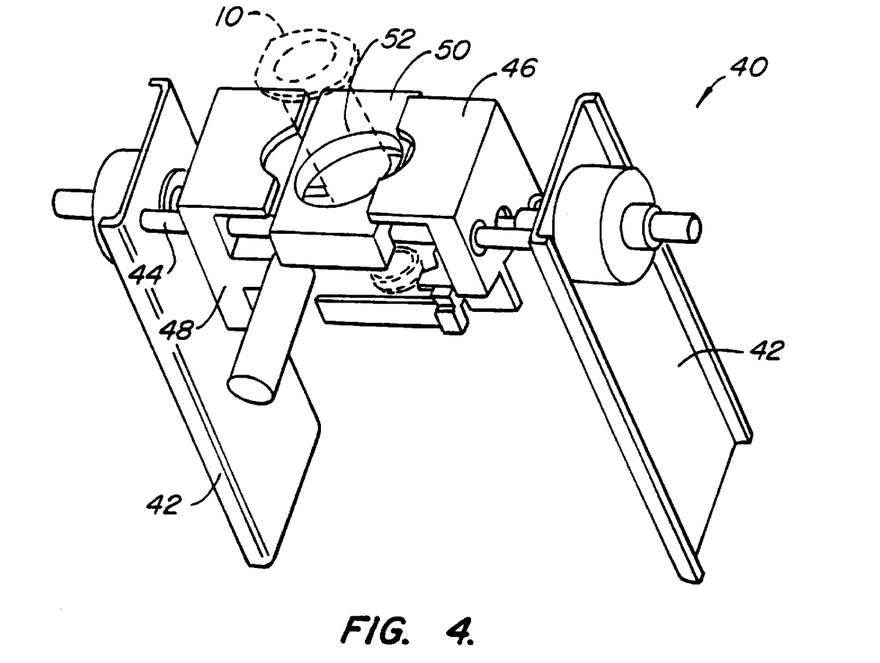
FIG. 4 is an isometric view of a blood separation driver constructed in accordance with the principles of the present invention.
Figure 5:
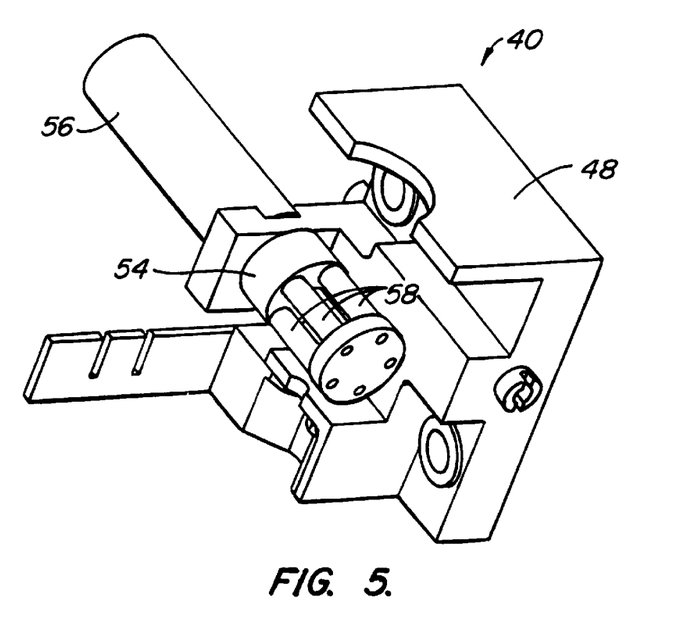
FIG. 5 is a detailed view of the peristaltic drive wheel and clamping element which form a part of the blood separation driver of FIG. 4.

To dispense blood with the blood dispensing system, a lower outlet dispensing assembly is employed with the blood dispensing device of the blood dispensing system. One embodiment of such a dispensing assembly is shown in FIG. 3A as dispensing assembly 19. The dispensing assembly 19 may be secured to an outlet end of the flexible tube 12 in a variety of ways, including as described above for the blood separation device. The dispensing assembly 19 further includes an outlet port at its base, such as, for example, the outlet port 36 shown in FIG. 3A, to permit outflow of whole or pre-filtered blood (or plasma that has already been separated from whole blood) from the blood dispensing device and direct transfer of such blood to a desired assay device or substrate.

With the dispensing assembly 19, the dispensing system functions in manner analogous to that described above for the blood separation device, except that no filtering process is conducted (as when the filter assembly 18 is used with the blood separation device). The dispensing assembly 19 is releasably captured in the blood dispensing driver in a manner similar to that discussed above in connection with the blood separation device and filter assembly 18. The lower portion of assembly 19 is removably captured in the blood dispensing driver (in the manner in which it is captured in the blood separation driver) by bringing the two opposed clamping elements 46 and 48 together. See, e.g., FIG. 7. In this way, the flexible tube 12 is anchored at both its inlet end (via the collar 50) and its outlet end (via capture of the dispensing assembly). The flexible tube will be held generally in place as it is captured between rollers 58 of drive wheel 54 and the arcuate recess 60 of clamp 46. When the drive wheel 54 is rotated, as shown in one embodiment by the arrow in FIG. 8 (as when assembly 18 is used with the blood separation device), peristaltic force induces blood from a blood collection (BC) device to flow through tube 12 and out from port 36 of assembly 19. When a desired volume of blood has been dispensed, rotation of drive wheel 54 can be stopped, opposed clamping elements 46 and 48 are moved apart, and the assembly comprising the blood collection device (BC) and blood dispensing device 10 is removed from the driver.

In another embodiment of the present invention, to dispense blood with the blood dispensing system, the filter elements of filter assembly 18, which include individual glass fiber layers 26, 28, 30, and the size-exclusion membrane 31 below the glass fiber layers (which are typically used with the blood separation device) are removed. Such filter elements are removed from the filter assembly 18 by opening the two separable halves 32 and 34 of filter assembly 18. Filter assembly 18 is then re-assembled without the filter elements. The resulting assembly functions as a dispensing assembly. As described above with regard to the blood separation device, such dispensing assembly may be secured to the outlet end of flexible tube 12 and may further include an outlet port 36 at its base to permit outflow of whole or pre-filtered blood (or plasma that has already been separated from whole blood) from the blood dispensing device and direct transfer of such blood to a desired assay device or substrate.

As noted above, with the filter elements removed from the filter assembly 18, the resulting assembly functions as a dispensing assembly. As with the filter assembly 18, the dispensing assembly can be releasably captured in the blood dispensing driver in a manner similar to that described in connection with the blood separation device. The lower portion of dispensing assembly is removably captured in the blood dispensing driver in the manner in which it is captured in the blood separation driver by bringing opposed clamping elements 46 and 48 together. See, e.g., FIG. 7. In this configuration, the flexible tube 12 is anchored at both its inlet end (via collar 50) and its outlet end (via capture of the dispensing assembly). The flexible tube will be held generally in place as it is captured between the rollers 58 of drive wheel 54 and the arcuate recess 60 of clamp 46. By rotating the drive wheel 54 (see, e.g., the arrow in FIG. 8, as when the filter assembly is employed), the resulting peristaltic force induces blood from a blood collection device (BC) to flow through tube 12 and out from port 36 of the dispensing assembly. When a desired volume of blood has been dispensed, rotation of the drive wheel 54 can be stopped, the opposed clamping elements 46 and 48 are moved apart, and the assembly of the blood collection device (BC) and blood dispensing device 10 is removed from the driver.

The present invention also provides methods for dispensing whole or filtered blood (or plasma) using the blood dispensing system. In one aspect, a method comprises providing a blood dispensing device having a flexible tube with an inlet end, an outlet end, and a blood flow lumen therebetween and a needle structure having a lumen which is disposed at the inlet end of the tube. Blood flowing from the blood flow lumen passes through the outlet end of the flexible tube. The method further comprises providing a blood dispensing driver which comprises a frame, a clamping assembly, and a peristaltic drive wheel. The clamping assembly includes two opposed clamping elements at least one of which is translatably coupled to the frame for translating said clamping element to selectively secure the blood dispensing device. The inlet end of the flexible tube is connected to a receptacle for blood so that blood flows into an internal lumen of the tube, and the blood dispensing device is removably secured in the dispensing driver by using the clamping assembly. By directing blood from the outlet end of the flexible tube through the outlet end of the tube, blood is dispensed. After a desired volume of blood has been dispensed, the intact assembly of the blood dispensing device and receptacle may be removed and disposed to minimize the risk of inadvertent blood loss. The dispensed blood may be transferred to an assay device or substrate.

Although the foregoing invention has been described in some detail by way of illustration and example, for purposes of clarity of understanding, it will be obvious that certain changes and modifications may be practiced within the scope of the appended claims.

What is claimed is:

1. A blood dispensing driver comprising:

a frame;

a clamping assembly on the frame for removably securing a blood dispensing device comprising a flexible tube having an inlet end and an outlet end, wherein said clamping assembly comprises first and second opposed clamping elements that are translatably coupled to the frame for removably securing the flexible tube in the blood dispensing driver;

a peristaltic drive wheel mounted on the first clamping element to engage the flexible tube between the drive wheel and the second clamping element when the blood dispensing device is secured in the clamping assembly, wherein rotation of the drive wheel induces blood to flow from the inlet end to the outlet end of the flexible tube, causing blood to be dispensed;

wherein the frame comprises a collar for supporting the inlet end of the flexible tube; and wherein the frame further comprises one or more rods which extend laterally from the collar, wherein at least one of the opposed clamping elements is translatable mounted on the rods, and wherein the dispensing driver further comprises at least one motor for translating one or both of the clamping elements to selectively secure and release the flexible tube when placed in the collar.

2. The blood dispensing driver as in claim 1, wherein the second clamping element has an arcuate surface which is aligned with the drive wheel, wherein the flexible tube is captured between the drive wheel and the arcuate surface.

3. The blood dispensing driver as in claim 1, wherein the drive wheel comprises a plurality of peripherally spaced-apart rollers.

4. A blood dispensing system comprising:

a blood dispensing device including a flexible tube having an inlet end and an outlet end and a needle structure at the inlet end of the tube;

a blood dispensing driver including a frame and a clamp mounted on the frame for removably securing the blood dispensing device, wherein said clamp comprises first and second opposed clamping elements, wherein at least one of the clamping elements is translatably coupled to the frame for translating said clamping element to selectively secure the blood dispensing device, and a peristaltic drive wheel on the frame which engages an exterior surface of the flexible tube to pass blood through a lumen thereof when the tube is secured in the clamp; wherein the frame comprises a collar for supporting the flexible tube, and wherein the frame further comprises one or more rods, which extend laterally from the collar, wherein at least one of the clamping elements is translatable mounted on the rods, and wherein the blood dispensing driver further comprises at least one motor for translating one or both of the clamping elements to selectively secure and release the flexible tube when placed in the collar.

5. The blood dispensing system as in claim 4, wherein the flexible tube has a length between the inlet end and the outlet end in the range from 10 mm to 100 mm and a blood flow lumen having a diameter in the range from 0.5 mm to 5 mm.

6. The blood dispensing system as in claim 4, wherein the needle structure has an axial passage which is aligned with the blood flow lumen of the flexible tube.

7. The blood dispensing system as in claim 4, wherein the blood dispensing device further comprises a receptacle shield which is attached to the inlet end of the flexible tube and which surrounds the needle structure.

8. The blood dispensing system as in claim 7, wherein the shield has a length in the range from 20 mm to 70 mm and an internal diameter in the range from 15 mm to 30 mm.

9. The blood dispensing system as in claim 4, wherein the collar is arranged for supporting the inlet end of the flexible tube.

10. The blood dispensing system as in claim 4, wherein the drive wheel is mounted on the first clamping element and the second clamping element has an arcuate surface which is aligned with the drive wheel, wherein the flexible tube is captured between the drive wheel and the arcuate surface.

11. The blood dispensing system as in claim 4, wherein the drive wheel comprises a plurality of peripherally spaced-apart rollers.

12. A blood dispensing system comprising:

a blood dispensing device including a flexible tube having an inlet end and an outlet end, wherein the inlet end of the tube has a needle structure; and a blood dispensing driver including:

a frame, wherein the frame comprises a collar for supporting the inlet end of the flexible tube and one or more rods which extend laterally from the collar;

a clamp for removably securing the blood dispensing device, wherein said clamp comprises first and second opposed clamping elements at least one of which is translatably mounted on the rods;

a peristaltic drive wheel which is mounted on at least one of the clamping elements and engages an exterior surface of the flexible tube to pass blood through a lumen thereof when the tube is secured in the clamp; and at least one motor for translating one or both of the clamping elements to selectively secure and release the flexible tube when placed in the collar.

13. The blood dispensing system as in claim 12, wherein one of the clamping elements has an arcuate surface which is aligned with the drive wheel, wherein the flexible tube is captured between the drive wheel and the arcuate surface.

* * * * *